(12) United States Patent
Komatani et al.

(10) Patent No.: US 6,762,834 B2
(45) Date of Patent: Jul. 13, 2004

(54) ELEMENT ANALYZER

(75) Inventors: Shintaro Komatani, Kyoto (JP); Yasushi Hirata, Kyoto (JP)

(73) Assignee: Horiba Ltd., Kyoto (JP)

( * ) Notice: Subject to any disclaimer, the term of this patent is extended or adjusted under 35 U.S.C. 154(b) by 0 days.

(21) Appl. No.: 10/367,877

(22) Filed: Feb. 19, 2003

(65) Prior Publication Data

US 2003/0156282 A1 Aug. 21, 2003

(30) Foreign Application Priority Data

Feb. 19, 2002 (JP) .................................. 2002-041132
Mar. 15, 2002 (JP) .................................. 2002-072734

(51) Int. Cl.[7] .................... G01J 3/30; G01N 25/26; G01N 35/02
(52) U.S. Cl. ................... 356/315; 436/48; 436/160; 422/78
(58) Field of Search ................ 356/315; 436/48, 436/49, 54, 62, 63, 155, 160; 422/78, 79, 80

(56) References Cited

U.S. PATENT DOCUMENTS 6,007,777 A * 12/1999 Purcell et al. ................ 422/80
6,248,217 B1 * 6/2001 Biswas et al. ........... 204/157.4

FOREIGN PATENT DOCUMENTS

JP          406308111 A  * 11/1994  .......... G01N/30/88

* cited by examiner

Primary Examiner—Frank G. Font
Assistant Examiner—Layla Lauchman
(74) Attorney, Agent, or Firm—Sughrue Mion, PLLC

(57) ABSTRACT

An element analyzer D comprises a combustion section 1 for burning a sample S, a sample injection member 2 for injecting the sample S into the combustion section 1, and a detection section 29 for measuring a gasified sample formed by burning the sample S in the combustion section 1. The element analyzer D further includes a cleaning-agent injection member 2 for injecting a cleaning agent W into the combustion section 1.

9 Claims, 6 Drawing Sheets

ELEMENT ANALYZER

FIELD OF THE INVENTION

The present invention relates to an element analyzer.

DESCRIPTION OF THE PRIOR ART

There has been known a fuel-sulfur analyzer using a combustion-type UV-excitation method as one type of element analyzers. This type of fuel-sulfur analyzer comprises a combustion section for burning a sample.

In the combustion-type fuel-sulfur analyzer, a sample is injected into and burnt in the combustion section to gasify the sample, and the gasified sample is transferred to a detection section to determine a sulfur content of the sample.

The combustion-type fuel-sulfur analyzer generally includes a sample injection member for injecting a sample into the combustion section. When the sample injection member is composed of an auto-sampler including a syringe and a needle, a sample is first sucked in the syringe and the needle, and then the needle is moved toward the combustion section to discharge or inject the sucked sample into the combustion section.

However, when the sample is injected into the combustion section, a part of the injected sample can be attached onto a relatively low-temperature portion of the combustion section. The attached sample will be vaporized or gasified bit by bit in a subsequent measurement likely to cause an adverse affect on the resulting measured value.

On the other hand, in view of eliminating an adverse affect from a liquid sample used in a previous measurement, it has been contemplated to run a cleaning liquid through the needle and the syringe so as to clean the inner walls of the syringe and the needle. However, this method is still involved in a problem of the above adverse affect because it cannot clean the outer periphery of the needle on which some of the liquid sample has been attached during the previous measurement.

From this point of view, the combustion-type fuel-sulfur analyzer may be provided with a cleaning vessel to be filled with a cleaning liquid. In this case, the needle is immersed in the cleaning vessel to clean the outer periphery of the needle. However, this method has involved a cumbersome and time-consuming operation of manually replacing the liquid in the cleaning vessel at certain intervals. In addition, if the needle is desirably cleaned with a newly replaced cleaning liquid for each measurement, the operation of replacing the cleaning liquid should be carried out as a preparatory for each measurement.

SUMMARY OF THE INVENTION

In view of the above problems, it is therefore an object of the present invention to provide an element analyzer capable of facilitating a high-precision measurement without adverse affect from a sample used in a previous measurement.

In order to achieve the above object, according to a first aspect of the present invention, there is provided an element analyzer including a combustion section for burning a sample, a sample injection member for injecting the sample into the combustion section, and a detection section for measuring a gasified sample formed by burning the sample in the combustion section. Further, the element analyzer comprises a cleaning-agent injection member for injecting a cleaning agent into the combustion section.

The element analyzer according to the first aspect of the present invention can inject the cleaning agent from the cleaning-agent injection member into the combustion section and remove contaminations due to the sample attached on the combustion section so that a high-precision measurement can be performed without adverse affect from a sample used in a previous measurement.

According to a second aspect of the present invention, there is provided an element analyzer including a combustion section for burning a sample, a sample injection member for injecting the sample into the combustion section, and a detection section for measuring a gasified sample formed by burning the sample in the combustion section. Further, the element analyzer comprises a cleaning-agent injection member for injecting a cleaning agent into the combustion section in a more upstream position relative to a position where the sample is injected into the combustion section.

The element analyzer according to the second aspect of the present invention can inject the cleaning agent from the cleaning-agent injection member into the combustion section in a more upstream position relative to a position where the sample is injected into the combustion section. Thus, the sample attached on the combustion section can be more reliably removed.

In the above element analyzers, the sample injection member may serve as the cleaning-agent injection member. In this case or a case of using the sample injection member commonly as the cleaning-agent injection member, the measurement can be performed with a high degree of accuracy while removing contaminations, without adding any component serving as the cleaning-agent injection member.

Further, according to a third aspect of the present invention, there is provided an element analyzer including a combustion section for burning a sample, a sample injection member for injecting the sample into the combustion section, and a detection section for measuring a gasified sample formed by burning the sample in the combustion section. Further, the element analyzer comprises a cleaning vessel. The cleaning vessel includes a cleaning bath for receiving therein a cleaning liquid to be injected from the front end of the sample injection member inserted into the cleaning bath. The cleaning bath has a height allowing the outer periphery of the front end of the inserted sample injection member to be cleaned by the cleaning liquid injected into the cleaning bath. The cleaning vessel also includes a waste-liquid port for discharging the injected cleaning liquid of the cleaning bath at a flow volume less than that of the cleaning liquid to be injected from the sample injection member.

The element analyzer according to the second aspect of the present invention can fill the cleaning bath with the cleaning liquid up to a predetermined height, while a part of the cleaning liquid injected from the sample injection member is discharged from the waste-liquid port. Thus, the sample attached on the outer periphery of the front end of the sample injection member in a previous measurement can be effectively cleaned, and the outer periphery of the front end of the sample injection member can be cleaned with a cleanly refreshed cleaning liquid all the time.

Therefore, the sample attached on the outer periphery of the front end of the sample injection member during a process of sucking the sample in a previous measurement can be cleaned, thereby facilitating a high-precision element analysis without adverse affect from the sample used in the previous measurement.

BRIEF DESCRIPTION OF THE DRAWINGS

FIGS. 5(A) and (B) are schematic explanatory block diagrams showing the relationship between the cleaning vessel and a needle of the injection device, wherein FIG. 5(A) shows the state before the needle is inserted into the cleaning vessel and FIG. 5(B) shows the state during a cleaning process of the needle and a syringe of the injection device;

DETAILED DESCRIPTION OF THE PREFERRED EMBODIMENTS

Figure 1:
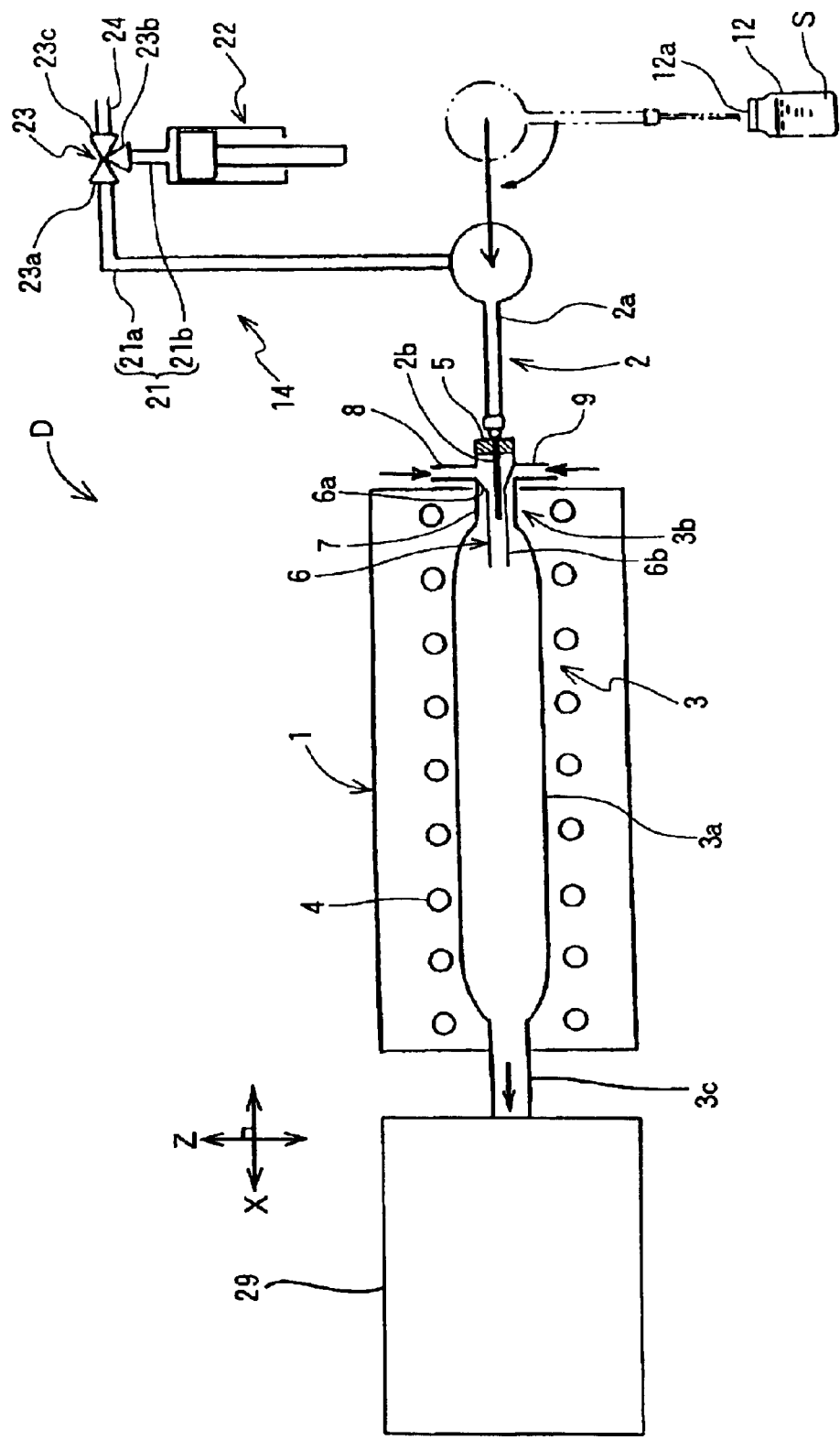
FIG. 1 is a schematic explanatory block diagram showing an element analyzer according to one embodiment of the present invention.
Figure 2:
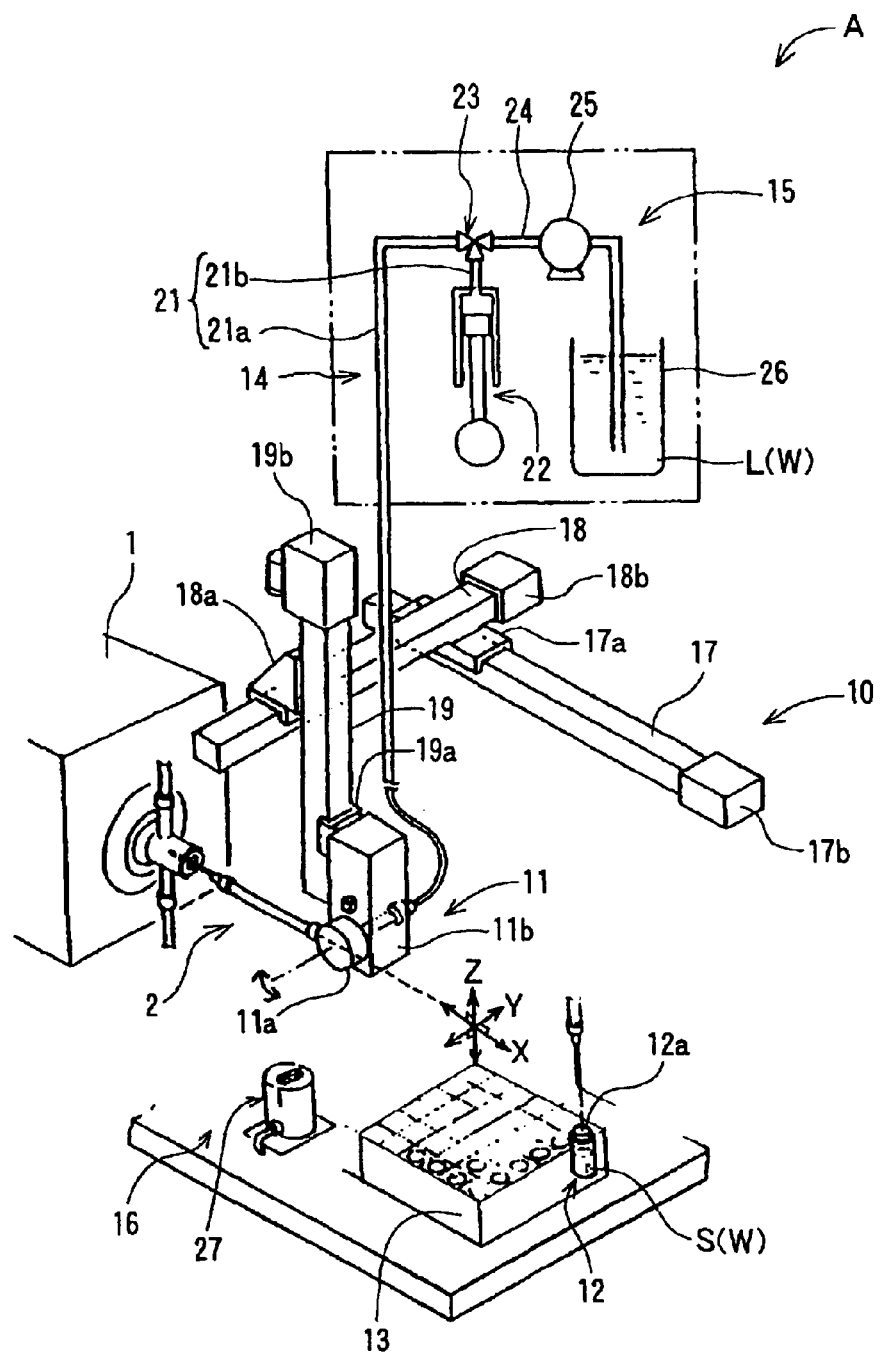
FIG. 2 is a schematic perspective block diagram showing an injection device of the element analyzer.
Figure 3:
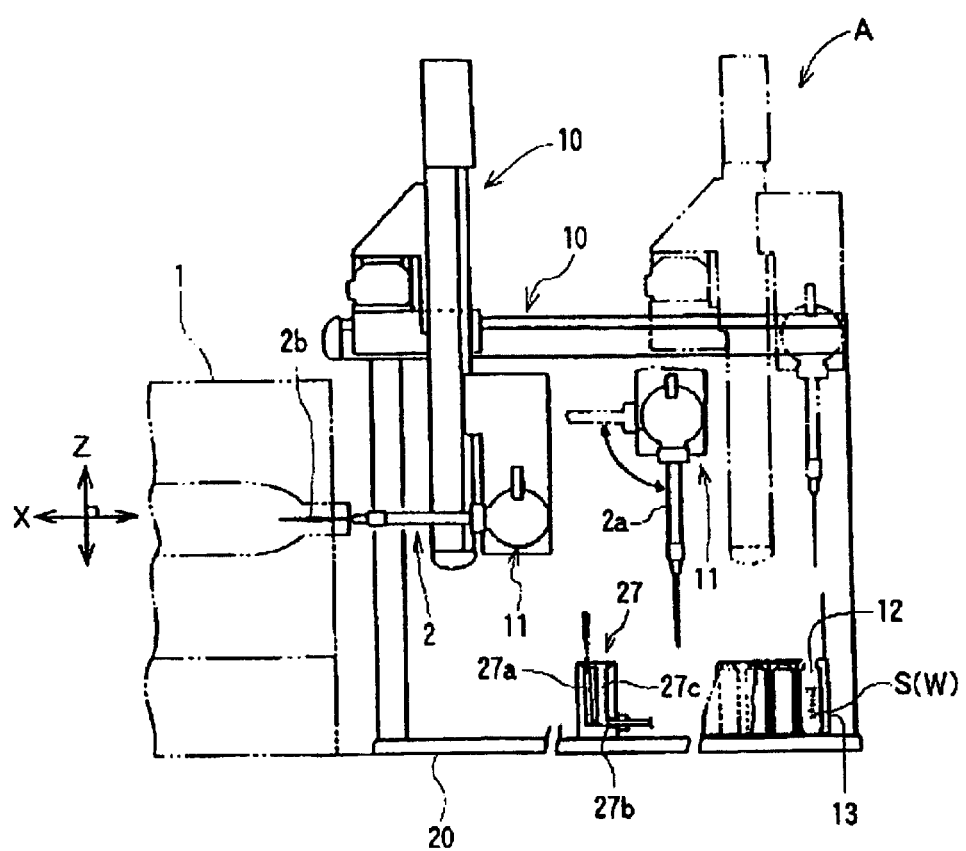
FIG. 3 is a schematic explanatory block diagram showing the injection device.

The present invention will now be described in detail with reference to the drawings. FIG. 1 is a schematic explanatory block diagram showing an element analyzer D according to one embodiment of the present invention. FIGS. 2 and 3 are respectively a schematic perspective block diagram and a schematic explanatory block diagram showing an injection device A serving as means for injecting a sample and a cleaning agent.

The element analyzer D may be a fuel-sulfur analyzer (X-ray fluorescence sulfur analyzer) using a combustion-type UV-excitation method (combustion UV-fluorescence method). As shown in FIG. 1, the element analyzer D comprises a combustion section 1 for burning a sample S, a sample injection member 2 for injecting the sample S into the combustion section 1, a detection section 29 for detecting a gas generated by burning the sample S in the combustion section 1, and a computer (not shown) for integrating signals received from the detection section 29 in response to the concentration of the gas to calculate the content of an element contained in the sample S.

The element analyzer D further includes the injection device A (described in detail later), which is an automatic sampling device or a so-called auto-sampler, located on an upstream side (rightward in FIG. 1) of the combustion section 1, in order to automate the entire process from a process of obtaining a given amount of the sample S by use of the sample injection member 2 to a process of injecting the obtained sample S into the combustion section 1. The sample injection member 2 is incorporated in the injection device A (see FIG. 2).

Between the combustion section 1 and the detection section 29, the element analyzer D additionally includes a dehydration section (not shown) for removing water or moisture contained in the gas generated in the combustion section 1 and a HC cutter (not shown) for removing unburnt hydrocarbons contained in the gas, which are arranged in this order from the upstream side.

The sample S may include a liquid-type sample (liquid sample) such as fuel oil.

The combustion section 1 is composed of a combustion furnace including a horizontal-type combustion tube 3 disposed to extend approximately in the horizontal direction, and heating means 4, such as a coil heater, disposed around the outer periphery of the combustion tube 3 to heat the combustion tube 3.

The combustion tube 3 is formed in a horizontally extending and flat shape having an approximately tubular (e.g. cylindrical) body portion 3a, an inlet portion 3b and an outlet portion 3c. The inlet and outlet portion 3b, 3c are located, respectively, on the upstream and downstream sides of the body portion 3a, and formed to have a smaller diameter than that of the body portion 3a.

The inlet portion 3b has a front edge (upstream edge) provided with a heat-resistant sealing member 5 for preventing a fluid such as air from communicating between the inside and outside of combustion tube 3 through the inlet portion 3b (or for hermetically or airtightly sealing the inlet portion 3b). The sealing member 5 may be a rubber plug made of heat-resistant rubber.

The inlet portion 3b is provided with a double-pipe structure composed of an inner tube 6 and an outer tube 7 which are in fluid communication with one another on the downstream side (leftward in FIG. 1). The inner tube 6 defines an interior space into which the sample injection member 2 is to be inserted. More specifically, the outer tube 7 is constructed by a part of the inlet portion 3a, and the inner tube 6 is disposed inside the outer tube 7 (the inlet portion 3b). The inner tube 6 includes, in order from the upstream edge, a taper surface portion 6a having a diameter gradually reduced in the downstream direction, and a thin tube portion 6b extending continuously from the downstream edge of the taper surface portion 6a and having an approximately constant diameter. The thin tube portion 6b is arranged and/or designed to have its downstream edge located more downstream than the downstream edge of the inlet portion 3b. The inner tube 6 may have a diameter of 0.8 mm, and the outer tube 7 may have a diameter of 1.0 mm.

A carrier-gas (mixed gas) supply passage 8 is connected to the upstream portion of the inner tube 6. The mixed-gas supply passage 8 can supply the interior space of the inner tube 6 with a carrier gas prepared by mixing oxygen with a base gas (e.g., air or inert gas such as Ar) consisting of a specific component nonreactive to oxygen and other than that intended to detect in the detection section 29. When the sample S is injected into the interior space of the inner tube 6, the supplied carrier gas will act to transfer the injected sample S through the interior space of the combustion-tube body portion 3a and the outlet portion 3c to the detection section 29 located on the downstream side of the combustion section 1. The base gas consists of one or more components having no adverse affect on the analysis in the detection section 29.

The carrier gas to be supplied from the carrier-gas supply passage 8 into the interior space of the inner tube 6 is not limited to the gas prepared by mixing oxygen with the base gas but may be a gas consisting only of oxygen.

Further, an oxygen supply passage 9 is connected to a space between the inner tube 6 and the outer tube 7. The oxygen supply passage 9 can supply oxygen to the interior space of the combustion tube 3 through the space between the inner tube 6 and the outer tube 7. The supplied oxygen in this way allows the interior space of the combustion tube 3 to be under oxygen atmosphere.

In order to increase the contact area with the sample S introduced in the interior space of the combustion tube 3 to provide effective heating of the introduced sample S, a number of chips (not shown) such as silica-glass chips are contained in the interior space of the combustion tube 3.

The heating means 4 is disposed to surround the combustion tube 3 and is operable to heat the combustion tube 3 so as to allow the interior space of the combustion tube 3 to be, for example, in the range of about 1000 to 1100° C.

The combustion tube 3 is formed in a flat shape and surrounded by the heating means 4 composed of the heater coil, as described above. This provides reduced temperature differences in the vertical, lateral and longitudinal directions of the interior space of the combustion tube 3, and thereby even the sample S falling down to the lower portion of the combustion tube 3 can be burnt without remaining in the combustion tube 3 in its unburnt state. Thus, the degradation in analytic accuracy otherwise caused by inadequate combustion can be advantageously suppressed.

As shown in FIG. 2, the injection device A comprises the sample injection member 2, a moving mechanism 10 for three-dimensionally moving the sample injection member 2, a rotating mechanism 11 for rotatably moving the sample injection member 2 about a horizontal axis, a vessel mount 13 for placing thereon a plurality of vessels 12, . . . , 12 each capable of reserving a liquid agent therein, actuating means 14 for actuating the sample injection member 2 to allow the sample injection member 2 to obtain (suck) a given amount of the sample S and inject the obtained sample S into the combustion section 1, liquid-agent supply means 15 for supplying a liquid agent to the sample injection member 2, not from the side of a needle 2b (as described in detail later) but from the side of a syringe 2a (as described in detail later), and cleaning means 16 for cleaning the sample injection member 2.

The sample injection member 2 includes the syringe 2a, and the needle 2b connected to one of the ends of the syringe 2a to provide fluid communication between the respective interior spaces of the needle 2b and the syringe 2a. The needle 2b may have an outer diameter of 1 mm and an inner diameter of 0.45 mm.

The moving mechanism 10 and the rotating mechanism 11 serve as means for moving the sample injection member 2 to the following three positions: a sampling position (as shown by a two-dot chain line in FIG. 1) where the tip of the needle 2b is immersed in the sample S so as to suck the sample S therein; a sample-injecting position (as shown by a solid line in FIG. 1) where the needle 2b is inserted in the interior space of the inner tube 6 of the combustion section 1 so as to inject the sample S into the combustion section 1; and a cleaning position (FIG. 5(B)) where the needle 2b is inserted into a cleaning bath 27a of an after-mentioned cleaning vessel 27.

The moving mechanism 10 comprises a first frame 17 extending in a direction getting close to and away from the combustion section 1 (hereinafter referred to as "X-direction"), a first sliding member 17a to be moved slidably along the first frame 17, a first motor case 17b disposed at one of the ends of the first frame 17 with a motor (not shown) housed therein and operable to slidably move the first sliding member 17a along the first frame 17, a second frame 18 extending in a direction perpendicular to the first frame 17 (hereinafter referred to as "Y-direction"), a second sliding member 18a to be moved slidably along the second frame 18, a second motor case 18b disposed at one of the ends of the second frame 18 with a motor (not shown) housed therein and operable to slidably move the second sliding member 18a along the second frame 18, a third frame 19 extending in a direction perpendicular to both the first and second frames 17, 18 (hereinafter referred to as "Z-direction"), a third sliding member 19a to be slidably moved along the third frame 19, and a third motor case 19b disposed at one of the ends of the third frame 19 with a motor (not shown) housed therein and operable to slidably move the third sliding member 19a along the third frame 19.

Any one of the frames 17, 18, 19 may be fixed to the sliding member to be moved slidably along either one of the remaining two frames, and the one remaining frame may be fixed to the sliding member to be moved slidably along the other remaining frame. In this embodiment, the X-direction and the Z-direction correspond to a horizontal direction and a vertical (upward and downward) direction, respectively. The X-direction and the Z-direction also correspond to the longitudinal direction and the lateral direction of the combustion section 1, respectively.

Further, in this embodiment, the first frame 17 is fixed to a housing 20 (see FIG. 3) of the injection device A, the second frame 18 being fixed to the first sliding member 17a to be moved slidably along the first frame 17, and the third frame 19 being fixed to the second sliding member 18a to be moved slidably along the second frame 18.

The rotating mechanism 11 includes a holding block 11a for holding the syringe 2a of the sample injection member 2, and a motor case block 11b housing therein a motor (not shown) for rotatably moving the holding block 11a at about 90-degree angles about a horizontal axis (e.g. the Y-axis). The motor case block 11b is fixed to the third sliding member 19a to be moved slidably along the third frame 19.

In response to the rotation of the holding block 11a, the sample injection member 2 held by the holding block 11a will be selectively moved between a first position parallel to the X-direction (hereinafter refereed to as "horizontal position") and a second position parallel to the Z-direction (hereinafter refereed to as "vertical position").

The vessel 12 is formed as a tubular vessel having an upper opening and a bottom. The opening is closed by a plug member 12a to seal the interior space of the vessel 12 hermetically. In this embodiment, the sample S is encased in the vessel 12. The plug member 12a is made of a material allowing the needle 2b to readily pierce therein and penetrate therethrough. Specifically, the plug member 12a may be a rubber or cork plug.

As shown in FIGS. 2 and 3, the vessel mount 13 is configured to allow the vessel 12 to be stably placed thereon without falling or overturning. The vessel mount 13 may be formed by using a tray having an upper opening and gridironed interior spaces.

The actuating means 14 includes a communication passage 21 in fluid communication with the syringe 2a of the sample injection member 2, and a syringe pump 22 to be communicated with the syringe 2a through the communication passage 21. That is, by actuating the syringe pump 22 in fluid communication with the syringe 2a, the sample injection member 2 can be operated to suck a given amount of a liquid agent from the needle 2b to hold the sucked liquid-agent therein and then inject the held liquid-agent from the tip of the needle 2b to the combustion section 1 (see FIG. 3).

As shown in FIGS. 1 and 2, a three-way solenoid valve 23 as a switching valve is provided in the communication passage 21 to divide the communication passage 21 into a first communication passage 21a between the three-way solenoid valve 23 and the syringe 2a of the sample injection member 2 and a second communication passage 21b between the three-way solenoid valve 23 and the syringe pump 22.

The liquid-agent supply means 15 includes a liquid-agent supply passage 24 to be communicated with the syringe 2a of the sample injection member 2 through the first communication passage 21a, a pump 25 such as a diaphragm pump to be communicated with the syringe 2a through the liquid-agent supply passage 24, and a liquid-agent reservoir vessel 26 for reserving a liquid agent into which the upstream portion of the liquid-agent supply passage 24 is immersed.

The liquid-agent supply passage 24 can communicate with the communication passage 21 (first communication passage 21a) through the three-way solenoid valve 23. That is, the three-way solenoid valve 23 is selectively switched between an actuation position allowing the second communication passage 21b to communicate with the first communication 21a and a liquid-agent supply position allowing the liquid-agent supply passage 24 to communicate with the first communication 21a.

More specifically, as shown in FIG. 1, the three-way solenoid valve 23 comprises a first valve portion 23a provided in the first communication passage 21a, a second valve portion 23b provided in the second communication passage 21b, and a third valve portion 23c provided in the liquid-agent supply passage 24. The activation position of the three-way solenoid valve 23 can be achieved by opening the first and second valve portions 23a, 23b and closing the third valve portion 23c. On the other hand, the liquid-agent supply position of the three-way solenoid valve 23 can be achieved by opening the first and third valve portions 23a, 23c and closing the second valve portion 23b.

Alternatively, three of two-way solenoid valves may be used as a substitute for the three-way solenoid valve 23. In this case, each of the first, second and third valve portions 23a, 23b, 23c will be composed of the two-way solenoid valve.

Figure 4:
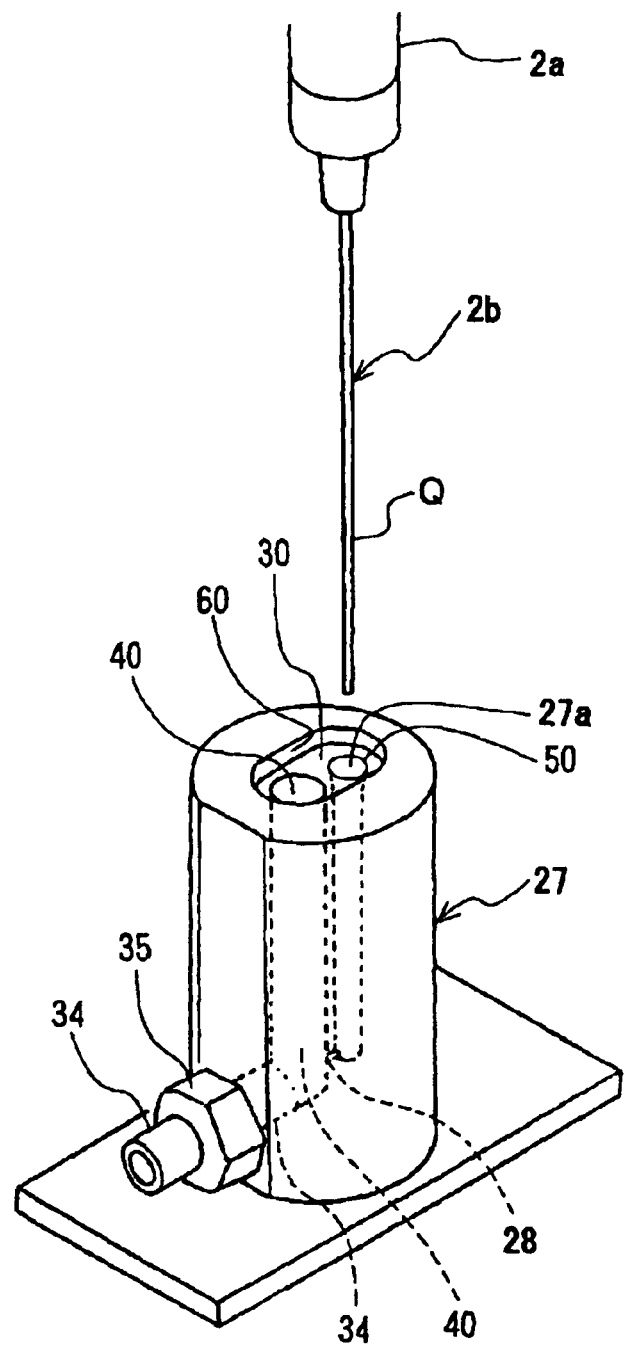
FIG. 4 is a schematic perspective view showing a cleaning vessel of the injection device.
Figure 5:
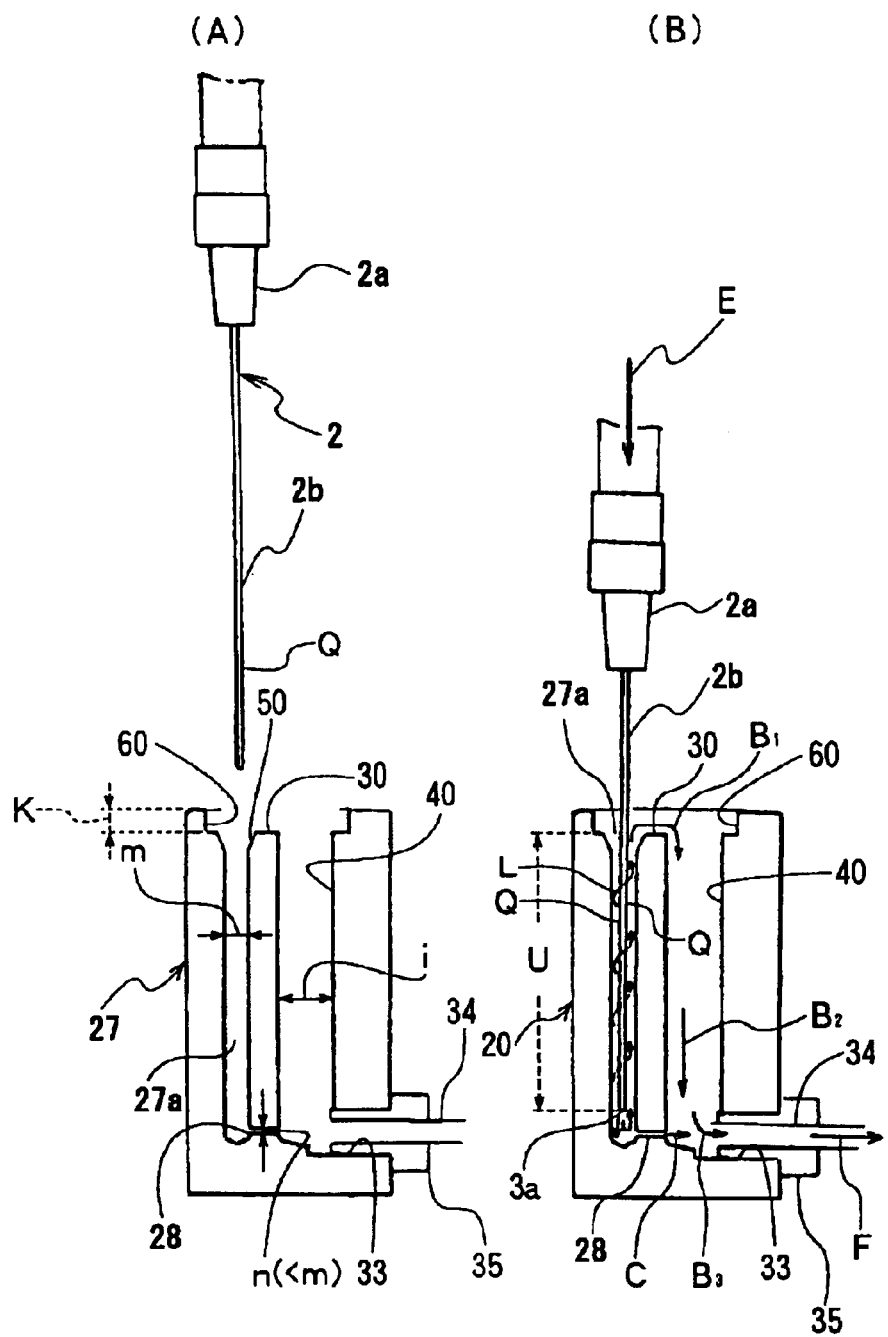

The cleaning means 16 includes the cleaning vessel 27 as shown in FIGS. 4 and 5. The cleaning vessel 27 may be used under the state where it is in fluid communication with the liquid-agent supply means 15.

The cleaning vessel 27 includes the approximately cylindrical cleaning bath 27a to be filled with the cleaning liquid for cleaning the outer periphery Q of the needle 2b, and an overflow bath 40 for discharging the cleaning liquid which has overflowed from the cleaning bath 27a. The cleaning bath 27a may be formed as a vertically extending elongated hole having a circular cross section. Further, the upper end of the cleaning vessel 27 is formed with a concave portion 60 having a depth K. The concave portion 60 has a bottom serving as an overflow surface 30 defining the respective uppermost openings or inlets of the cleaning bath 27a and the overflow bath 40. The cleaning vessel 27 further includes a discharge port 33 which is formed at the lowermost position of its side wall, and a waste-liquid port 28 which is formed at the lowermost position of its partition wall between the cleaning bath 27a and the overflow bath 40 and at approximately the same position in height as that of the discharge port 33. The cleaning liquid injected from the needle 1 into the cleaning bath 27a of the cleaning vessel 27 can be discharged directly toward the overflow bath 40 through the waste-liquid port 28. In this embodiment, each of the overflow bath 40, the waste-liquid port 28 and the discharge port 33 is formed as a circular hole.

The waste-liquid port 28 in this embodiment is designed to discharge the cleaning liquid from the cleaning bath 27a toward the overflow bath 40 at a flow volume less than that of the injected cleaning liquid from the sample injection member 2 into the cleaning bath 27a. Specifically, when the cleaning liquid is passed through the syringe 2a and the needle 2b and injected from the tip of the needle 2b into the cleaning bath 27a of the cleaning vessel 27 at a flow volume greater than that of the cleaning liquid to be discharged from the waste-liquid port 28, a part of the injected cleaning liquid L (FIG. 5(B)) can remain at the cleaning bath 27a, and the cleaning bath 27a will be gradually filled with the injected cleaning liquid. Then, if the cleaning liquid is continuously injected from the tip of the needle 2b into the cleaning bath 27a, the level of the injected cleaning liquid will rise up to the overflow surface 30 and thereby the injected cleaning liquid will overflow from the cleaning bath 27a. Thus, this embodiment employs a structure for combining the overflowed cleaning liquid running over the overflow surface 30 and the discharged cleaning liquid from the waste-liquid port 28 together through the overflow bath 40 and then discharging the confluence of the cleaning liquid outside through a discharge pipe 34 connected to the discharge port 33 of the cleaning vessel 27. As already mentioned, the overflow surface 30 corresponds to the bottom having the depth K of the concave portion 60 formed at the upper end of the cleaning vessel 27. Thus, the overflowed cleaning liquid from the cleaning bath 27a can be held in the concave portion 60 and then discharged from the overflow bath 40 so as to prevent the overflowed cleaning liquid from running over outside from the upper end of the cleaning vessel 27. In FIGS. 4 and 5, the reference numeral 35 indicates a positioning joint for attaching the discharge pipe 34 onto the discharge port 33.

As seen in FIG. 5(B), in this embodiment, first, second and third overflowed-liquid flows $B_1$, $B_2$, $B_3$ are formed in the cleaning vessel 27 to discharge the overflowed cleaning liquid from the cleaning bath 27a. The respective overflowed-liquid flows $B_1$, $B_2$, $B_3$ are guided by the overflow surface 30 and the overflow bath 40. The first overflowed-liquid flow $B_1$ is a most-upstream flow among the overflowed-liquid flows $B_1$, $B_2$, $B_3$, the second overflowed-liquid flow $B_2$ being formed just downstream of the first overflowed-liquid flow $B_1$, and the third overflowed-liquid flow $B_3$ being formed just downstream of the second overflowed-liquid flow $B_2$. That is, the third overflowed-liquid flow $B_3$ is a most-downstream flow. The arrow C in FIG. 5(B) indicates the flow of the discharged cleaning liquid from the discharge port 28. This waste-liquid flow C is formed just downstream of the waste-liquid port 28. The waste-liquid flow C and the third overflowed-liquid flow $B_3$ are joined just upstream of the discharge port 33 and discharged as a discharge flow F through the discharge pipe 34. The arrow E in FIG. 5(B) indicates a cleaning-liquid flow in the syringe 2a.

In the present invention, the dimension of the waste-liquid port 28 and the height of the cleaning bath 27a are set such that an injection flow-volume T of the injected cleaning liquid from the tip of the needle 2b is greater than a waste-liquid flow-volume H of the discharged cleaning liquid from the waste-liquid port 28 to fill the cleaning bath 27a of the cleaning vessel 27 with the injected cleaning liquid so as to additionally clean the outer periphery Q of the needle 2b.

Further, in order to achieve a speedy cleaning process, the cleaning bath 27a of the cleaning vessel 27 in this embodiment has a reduced diameter to allow the level of the injected cleaning liquid in the cleaning bath 27a of the cleaning vessel 27 to be increased at a high speed while minimizing the volume of the cleaning liquid to be injected into the cleaning bath 27a. In this embodiment, the diameter m of the cleaning bath 27a of the cleaning vessel 27 is set, for example, at 2 mm, and at least the injection flow-volume T of the injected cleaning liquid from the tip of the needle 2b (cleaning-liquid injection flow-rate) and the diameter n (<m) of the waste-liquid port 28 are appropriately set such that the cleaning liquid is injected from the tip of the needle 2b at the injection flow-volume (cleaning-liquid injection flow-rate) T greater than the waste-liquid flow-volume (waste-liquid flow-rate) H to allow the difference between the injected cleaning liquid and the discharged cleaning liquid from the waste-liquid port 28 to be increasingly accumulated in the cleaning bath 27a. In this case, the diameter n of the waste-liquid port 28 is set to be smaller than the diameter m of the cleaning bath 27a, for example, at 1 mm. Preferably, the injection flow-volume (cleaning-liquid injection flow-rate) T from the tip of the needle 2b is set in the range of about 4 to 8 milliliter/minute. As above, in the present invention, the cleaning bath 27a of the cleaning vessel 27 is filled with the cleaning liquid by appropriately setting the diameter m of the cleaning bath 27a, the diameter n of the waste-liquid port 28, the injection flow-volume (cleaning-liquid injection flow-rate) T, and the height of the cleaning bath 27a while considering the relationship between the length of the needle 2b to be inserted into the cleaning bath 27a and each of these dimensions, so that the outer periphery Q of the needle 2b can be additionally cleaned with the cleaning liquid filled in the cleaning bath 27a.

In this embodiment, the diameter i of the overflow bath 40 is set at 5 mm. The overflow bath 40 does not have the requirement for accumulating the cleaning liquid as in the cleaning bath 27a of the cleaning vessel 27 because of difference in purpose between the overflow bath 40 and the cleaning bath 27a, and thereby the diameter i can be freely set depending on circumstances.

The cleaning of the outer periphery Q of the needle (the front end of the sample injection member) herein means to clean the needle 2b (the front end of the sample injection member) in a certain height range corresponding to an immersed depth U of the needle 2b which has been immersed below the liquid level of the liquid sample S reserved in the sample vessel 12 as shown in FIGS. 2 and 3 during a sucking process of sucking or introducing the liquid sample S of the sample vessel 12. That is, in the embodiment as shown in FIG. 5(B), the distance between the tip of the needle 2b and the overflow surface 30 at most is set to be equivalent to the immersed depth U of the needle 2b serving as the front end of the sample injection member. Thus, if the needle 2b is immersed in a greater immersed depth U during the sucking process, it is easily appreciated that the depth of the cleaning bath 27a in FIG. 5(B) should be increased accordingly. What is important is that the dimension (height) of the cleaning vessel 27 and the cleaning bath 27a used in the present invention may be designed to be variable depending on the immersed depth U during the sucking process of the needle 2b for introducing the liquid sample.

As shown in FIG. 5(A), the inlet portion 50 of the cleaning bath 27a of the cleaning vessel 27 may be formed in a tapered shape having a downward taper. In this case, the downward tapered inlet portion 50 will fulfill a guide function of allowing the needle 2b to be readily inserted into the cleaning bath 27a even if the difference between the outer diameter of the needle 2b and the diameter of the cleaning bath 27a is small and/or an insertion process of inserting the needle 2b into the cleaning bath 27a is performed with some displacement. Further, the waste-liquid port 28 may be formed to have not only an evenly reduced diameter but also a configuration provided with a protrusion or orifice for controlling the flow volume of the discharged cleaning liquid after the injection/cleaning process.

In the cleaning process of cleaning the sample injection member 2 by use of the cleaning means or a cleaning-agent receiving member 16 having the cleaning vessel 27 constructed as above, the cleaning liquid L such as ethanol used for cleaning the inner wall surface of the syringe 2a and the inner and outer wall surfaces of the needle 2b is reserved in the liquid-agent reservoir vessel 26 of the liquid-agent supply means 15 in advance as shown in FIG. 2, and the needle 2b of the sample injection member 2 is inserted into the cleaning bath 27a.

Then, the three-way solenoid valve 23 is switched to the liquid-agent supply position, and the pump 25 is actuated to transfer the cleaning liquid L of the liquid-agent reservoir vessel 26 into the sample injection member 2 from the side of the syringe 2a. After passing through the respective interior spaces of the syringe 2a and the needle 2b, the cleaning liquid L is injected from the tip of the needle 2b into the cleaning bath 27a. During this process, the cleaning liquid L is accumulated in the cleaning bath 27a, and the level of the cleaning liquid L in the cleaning bath 27a will rise up to a given height, because the waste-liquid port 28 of the cleaning vessel 27 is set to discharge the cleaning liquid from the cleaning bath 27a at a flow volume less than the injection flow volume from the sample injection member 2, or a flow volume of the cleaning liquid L to be supplied from liquid-agent reservoir vessel 26 into the cleaning bath 27a is arranged to be greater than a flow volume of the cleaning liquid L to be discharged from the waste-liquid port 28. Thus, the outer wall of the needle 2b can be additionally cleaned (FIG. 5(B)).

The detection section 29 includes irradiation means (not shown) for emitting an ultraviolet light (wavelength: 215 nm) toward the sample gas transferred from the combustion section 1, and detection means (not shown) for detecting a light (fluorescence) generated by the irradiation of the ultraviolet light. The detection means may be composed of a photomultiplier (PMT).

The process of the element analyzer D constructed as above will be described below. Firstly, a sampling process of obtaining a given amount of sample S by use of the sample injection member 2 will be described. This sampling process is performed by using the injection device A. More specifically, the sampling process comprises a first step of moving the sample injection member 2 to a position opposed to the vessel 12 reserving the sample S therein, a second step of immersing the needle 2b of the sample injection member 2 in the sample S of the vessel 12, and a third step of sucking a given amount of the sample S in the sample injection member 2 through the needle 2b.

In the first step, the sample injection member 2 is moved by the moving mechanism 10 and the rotating mechanism 11. After the completion of the movement, the sample injection member 2 is in a position where the needle 2b can be inserted into the vessel 12 (a position where the needle 2b extends in a vertically downward direction, in this embodiment).

In the second step, the moving mechanism 10 moves the sample injection member 2 in a direction getting close to the vessel 12 to allow the needle 2b to be penetratingly inserted into the plug member 12a of the vessel 12 and immersed in the sample S of the vessel 12.

In the third step, the three-way solenoid valve 23 is switched to the actuation position, and the syringe pump 22 is activated to suck the given amount of the sample S in the sample injection member 2.

Secondary, a sample injection process of injecting the sample S into the combustion section 1 by use of the sample injection member 2 will be described. This sample injection process is also performed by using the injection device A. More specifically, the sample injection process comprises a fourth step of moving the sample injection member 2 to a position opposed to the combustion section 1, a fifth step of inserting the needle 2b of the sample injection member 2 into the combustion section 1, and a sixth step of injecting the given amount of the sample S from the needle 2b into the combustion section 1.

In the fourth step, the sample injection member 2 is moved by the moving mechanism 10 and the rotating mechanism 11. After the completion of the movement, the sample injection member 2 is in a position where the needle 2b can be inserted into the combustion section 1 (a position where the needle 2b extends in a horizontal direction, in this embodiment).

In the fifth step, the moving mechanism 10 moves the sample injection member 2 in a direction getting close to the combustion section 1 to allow the needle 2b to be penetratingly inserted into the sealing member 5 of the inlet portion 3b and inserted into the combustion section 1.

In the sixth step, the three-way solenoid valve 23 is maintained in the actuation position, and the syringe pump 22 is activated to inject the given amount of the sample S into the combustion section 1.

Thirdly, a combustion process between the introduction of the sample S into the combustion section 1 and the transfer of the sample gas to the downstream side of the combustion section 1 will be described. This combustion process comprises a seventh step of transferring the injected sample S from the tip of the needle 2b of the sample injection member 2, to the body portion 3a of the combustion tube 3 through the thin tube portion 6b of the inner tube 6b, an eighth step of burning the sample S in the interior space of the body portion 3a, and a ninth step of transferring the burnt sample S to the downstream side of the combustion tube 3.

In the seventh step, the injected sample S from the tip of the needle 2b inserted in the interior space of the thin tube portion 6b of the inner tube 6 is transferred through the interior space of the thin tube portion 6b to the body portion 3a of the combustion tube 3 by the carrier gas supplied from the carrier-gas supply passage 8 connected to the upstream portion of the inner tube 6.

In the eighth step, since the interior space of the body portion 3a of the combustion tube 3 is kept under oxygen atmosphere by the oxygen supplied from the oxygen supply passage 9 connected to the upstream end of the combustion section 1, the sample S is reliably burnt and gasified. In this embodiment, sulfur components of the sample S introduced into the combustion tube 3 is oxidized in the interior space of the combustion section 1 kept under oxygen atmosphere and is converted into sulfur dioxide ($SO_2$). In the ninth step, the gasified sample or sample gas is transferred downstream through the combustion section 1 together with the carrier gas.

Following the combustion process, in the detection section 29 located at a downstream side of the combustion section 1, the $SO_2$ ($SO_2$ molecules) in the sample gas is irradiated with an ultraviolet light (wavelength: 215 nm). This irradiation brings a part of the $SO_2$ molecules in an exited state, and the exited molecules immediately transit to a ground state because the molecules in the excited state are highly unstable. The photomultiplier (PMT) detects a light (fluorescence) generated in proportion to the difference in energy between the exited and ground states, and the detected signals are integrated to determine a total $SO_2$ amount. An $SO_2$ concentration is measured based on the $SO_2$ amount and the volume and density of the sample S, and then the determined $SO_2$ concentration is converted into a mass concentration to obtain the concentration of sulfur components of the sample S to be analyzed.

After the above measurement, the sample injection member 2 itself is cleaned by the cleaning means 16. The cleaning process of cleaning the sample injection member 2 by use of the cleaning means 16 has been described above, and a repeated description thereof will be omitted.

In the element analyzer D, as constructed above, the sample injected into the combustion section 1 can be attached onto a relatively low-temperature portion of the combustion section 1. Thus, the combustion section 1 is to be cleaned up so as to remove the attached sample S onto the inside of the combustion section 1.

More specifically, in a process of cleaning the combustion section 1, the element analyzer D is operable to inject a cleaning agent W into the combustion section. For this purpose, the element analyzer D includes means for injecting the cleaning agent W into the combustion section 1, and the sample injection member 2 is used as the cleaning-agent injection means. The cleaning agent W may be injected into the combustion section 1 through the same steps as the aforementioned first to sixth steps. In that case, the cleaning agent W is reserved in the vessel 12 in advance.

The same material as the cleaning liquid L may be used as the cleaning agent W. Specifically, a liquid (cleaning liquid), such as water, or an alcohol, such as ethanol, may be used as the cleaning agent W. In view of risk or disadvantage caused by burning in the combustion section 1 and remaining as contaminations in combustion section 1, it would be desirable to use water as the cleaning agent W.

The process of supplying the cleaning agent W to the sample injection member 2 is not limited to the process of sucking the cleaning agent W from the vessel 12 and reserving it in the sample injection member 2 as in the aforementioned first to third steps. For example, based on the use of the liquid-agent supply means 15, the three-way solenoid valve 23 may be switched to the liquid-agent supply position, and the pump 25 may be activated to supply the cleaning agent W to the interior space of the sample injection member 2. In this case, the cleaning agent W is reserved in the liquid-agent reservoir vessel 26 in advance.

Figure 6A:
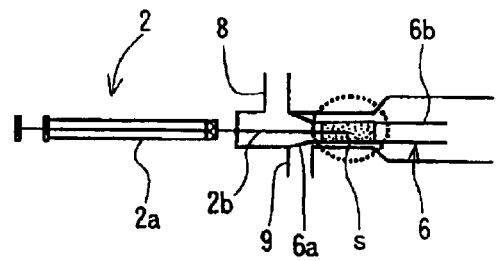
FIGS. 6(A), (B) and (C) are schematic explanatory partial block diagrams showing the element analyzer, respectively, during a measuring process, during a cleaning process of a combustion section and after the cleaning process.
Figure 6B:
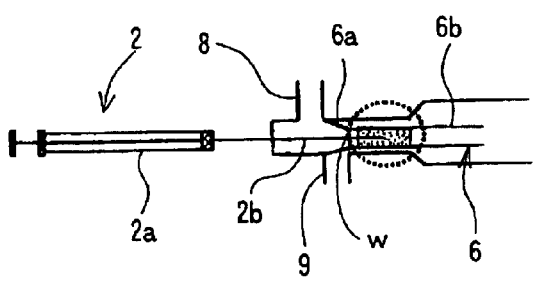
Figure 6C:
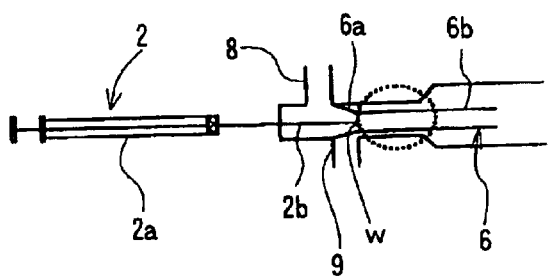

As shown in FIGS. 6(A) and 6(B), the element analyzer D is configured to inject the cleaning agent W from the tip of the needle 2b at a position w located about 5 cm upstream (leftward in FIG. 6) from a position s of the tip of the needle 2b for injecting the sample S, because the injected sample S from the tip of needle 2b cannot flow toward the downstream side (rightward in FIG. 6) of the combustion tube 3, due to the so-called capillary phenomenon, but flow into a space between the outer periphery of the needle 2b and the thin tube portion 6b of the inner tube 6 and consequently can be attached onto the inner periphery of the inner tube 2. The construction of differentiating the position w for injecting the cleaning agent W from the position s for injecting the sample S (i.e., locating the position w on the upstream side of the position s) provides an excellent advantage of cleaning and removing the attached sample S on the inner periphery of the inner tube 6, as shown in FIG. 6(C), and more particularly eliminating contaminations in the inner tube 6 (around the thin tube portion 6b) which has been left as an unsettled problem. In this embodiment, the number of times of the process of injecting the cleaning agent W is not limited. The cleaning agent W may be injected more than once depending on the concentration of the attached sample.

The element analyzer D constructed as above can reliably remove the attached sample S in the combustion section 1 to prevent an adverse affect caused by such an attached sample S to be vaporized or gasified bit by bit in a subsequent measurement, thereby achieving a high-precision measurement.

While the above embodiment employs the horizontal-type combustion tube 3 in the combustion section 1, the present invention is not limited to such a construction, but a vertical-type combustion tube 3 or a combustion tube 3 extending in the vertical direction instead of the horizontal direction may be used.

Further, while the above embodiment is configured to use the injection device A so as to inject the sample S from the sample injection member 2 into the combustion section 1, the present invention is not limited to such a construction, but an operator may manually inject the sample S from the sample injection member 2 into the combustion section 1 without automating the injection device A.

Further, while the above embodiment is configured to inject the cleaning agent from the sample injection member 2 into the combustion section 1, the present invention is not limited to such a construction, but an operator may manually inject the cleaning agent into the combustion section 1 by using a cleaning syringe without providing the injection device A.

Furthermore, while the above embodiment employs the fuel-sulfur analyzer (X-ray fluorescence sulfur analyzer) for analyzing sulfur components contained in the sample S as the element analyzer D, the present invention is not limited to such a construction, but an analyzer for detecting another component contained in the sample S, such as carbon, nitrogen or chlorine components other than sulfur components carbon, may be used as the element analyzer D.

As mentioned above, the present invention can provide an improved element analyzer capable of eliminating contaminations and performing a high-precision measurement.

What is claimed is:

1. An element analyzer, comprising:
   a combustion section for burning a sample;
   a sample injection member for injecting the sample into said combustion section;
   a detection section for measuring a gasified sample formed by burning the sample in said combustion section; and
   a cleaning-agent injection member for injecting a cleaning agent into said combustion section.

2. The element analyzer as defined in claim 1, wherein said sample injection member serves as said cleaning-agent injection member.

3. An element analyzer, comprising:
   a combustion section for burning a sample;
   a sample injection member for injecting the sample into said combustion section;
   a detection section for measuring a gasified sample formed by burning the sample in said combustion section; and
   a cleaning-agent injection member for injecting a cleaning agent into said combustion section in a more upstream position relative to a position where the sample is injected into said combustion section.

4. The element analyzer as defined in claim 3, wherein said sample injection member serves as said cleaning-agent injection member.

5. An element analyzer, comprising:
   a combustion section for burning a sample;
   a sample injection member for injecting the sample into said combustion section;
   a detection section for measuring a gasified sample formed by burning the sample in said combustion section; and
   a cleaning vessel for cleaning an outer periphery of a front end of said sample injection member, said cleaning vessel comprising:
   a cleaning bath for receiving therein a cleaning liquid to be injected from the front end of said sample injection member inserted into said cleaning bath, said cleaning bath having a height allowing the outer periphery of the front end of said inserted sample injection member to be cleaned by the cleaning liquid injected into said cleaning bath; and
   a waste-liquid port for discharging the injected cleaning liquid of said cleaning bath at a flow volume less than that of the cleaning liquid to be injected from said sample injection member.

6. The element analyzer as defined in claim 5, wherein said cleaning vessel includes an overflow bath for receiving therein and discharging therefrom the cleaning liquid running over from said cleaning bath.

7. The element analyzer as defined in claim 5, wherein said cleaning bath has an inlet portion for receiving therethrough the front end of said sample injection member, said inlet portion being formed in a tapered shape having a diameter increasing outward.

8. The element analyzer as defined in claim 6, wherein said cleaning bath has an inlet portion for receiving therethrough the front end of said sample injection member, said inlet portion being formed in a tapered shape having a diameter increasing outward.

9. The element analyzer as defined in either one of claims 1 to 8, wherein said sample injection member includes a needle and a syringe for sucking and/or injecting.

* * * * *